US00PP12177P2

(12) United States Plant Patent
Rabin

(10) Patent No.: US PP12,177 P2
(45) Date of Patent: Oct. 30, 2001

(54) PHALAENOPSIS PLANT NAMED 'DOROTHY APPLEGATE'

(75) Inventor: Mitch Rabin, Goulds, FL (US)

(73) Assignee: Twyford Plant Laboratories, Inc., Sebring, FL (US)

( * ) Notice: Subject to any disclaimer, the term of this patent is extended or adjusted under 35 U.S.C. 154(b) by 0 days.

(21) Appl. No.: 09/572,313

(22) Filed: May 18, 2000

(51) Int. Cl.[7] ..... A01H 5/00
(52) U.S. Cl. ..... Plt./311

(58) Field of Search ..... Plt./311

*Primary Examiner*—Bruce R. Campell
*Assistant Examiner*—Annette H. Para
(74) *Attorney, Agent, or Firm*—Foley & Lardner

(57) ABSTRACT

A new and distinct Phalaenopsis orchid variety named 'Dorothy Applegate' which produces flowers which are almost entirely covered with bright-pink stripes and spots over a white background. The flowers are carried on sturdy, upright, frequently branched spikes. Mature plants initiate spikes year round, regardless of season, and once in bloom, tend to remain in bloom. The plant grows very easily and quickly to marketable size.

2 Drawing Sheets

BACKGROUND OF THE INVENTION

The present invention comprises a new and distinct cultivar of Phalaenopsis orchid, hereinafter referred to by the cultivar name 'Dorothy Applegate'. The genus Phalaenopsis is a member of the family Orchidaceae.

Phalaenopsis comprises a genus of about 55 species of herbaceous perennials many of which, or the hybrids thereof, are suitable for cultivation in the home or greenhouse. Phalaenopsis is predominantly epiphytic or rock-dwelling, and is native to tropical Asia, Malay Archipelago and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

Phalaenopsis orchids, often referred to as 'Moth Orchids' in the horticultural trade, are frequently used to furnish cut flowers for the florist trade or sold as flowering potted-plants for home or interiorscape.

Phalaenopsis produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

Phalaenopsis orchids are typically propagated from seeds. Asexual propagation of Phalaenopsis is often done from off-shoots which frequently arise from the lower bracts of the inflorescence. The resulting plants are detached from the mother plant and may be planted in a suitable substrate.

The new cultivar is a product of a breeding program carried out by the inventor, Mitch Rabin. The new cultivar is a result of a self-pollination of an unnamed selection of Phalaenopsis×'Taida Modern' (unpatented) made in April of 1992.

The new cultivar is a seedling selected from seed produced by self-pollinating a plant that was produced by crossing an unnamed selection of Phalaenopsis with the Phalaenopsis cultivar 'Taida Modern' in April, 1992.

Asexual propagation by tissue culture, performed by the inventor in Sebring, Fla., was used to increase the number of plants for evaluation and has demonstrated that the combination of characteristics as here in disclosed for 'Dorothy Applegate' are firmly fixed and are retained through successive generations of asexual reproduction.

BRIEF DESCRIPTION OF THE INVENTION

The following traits have been repeatedly observed to be characteristics which in combination distinguish 'Dorothy Applegate' from generally available seedling-derived Phalaenopsis common in commercial cultivation:

1. Flowers are densely covered with bright-pink spots and stripes over a white background;

2. Petals have a distinctive wavy, white-bordered margin;

3. Inflorescence is short, frequently-branched and sturdy;

4. Plants grow quickly and begin flowering early producing marketable flowering plants in approximately 8 months; and;

5. Plants initiate spikes on mature plants year-round, regardless of season, and once in bloom, tend to remain in bloom.

The new cultivar 'Dorothy Applegate' differs from the parent cultivar 'Taida Modern' in that the flowers are larger, and have more pronounced undulations along the petals than those of 'Taida Modern'. In addition, the inflorescence of 'Dorothy Applegate' is larger, and more likely to branch than those of 'Taida Modern'.

'Dorothy Applegate' has not been observed under all possible environmental conditions. The phenotype may vary significantly with variations in environment such as temperature, light intensity, fertilization and daylength without any change in the genotype. The following observations, measurements and values describe plants grown in Goulds, Fla. under greenhouse conditions which closely approximate those generally used in horticultural practice.

Perhaps the closest commercial comparison to 'Dorothy Applegate' can be made to seedling-derived Phalaenopsis which are heterogeneous genetically, and typically lack uniformity in growth vigor, habit, and flower quality. Since the reference point has inconsistent characteristics, a direct comparison for 'Dorothy Applegate' is not available. 'Dorothy Applegate' is a single genotype asexually propagated via tissue culture, thus its combined horticultural properties listed above are uniform and predictable.

BRIEF DESCRIPTION OF THE DRAWING

The accompany photographic illustrations show typical plant and flower characteristics of an 11-cm pot plant of 'Dorothy Applegate' with colors being as true as possible with illustrations of this type.

Sheet 1 is a top perspective view of a plant of 'Dorothy Applegate'.

Sheet 2 is a close up view showing the characteristics of the flowers. The photographs were taken approximately 6 months after planting a 12-week-old liner obtained by tissue culture and grown under appropriate growing conditions.

DETAILED BOTANICAL DESCRIPTION

All color references are measured against The Royal Horticultural Society (R.H.S.) Colour Chart. Colors are approximate as color depends on horticultural practices such as light level and fertilization rate, among others, without, however any change in genotype.

Origin: Seedling selected from a self-pollination of Phalaenopsis×'Taida Modern'.

Classification: Phalaenopsis c.v. 'Dorothy Applegate'.

Propagation: Asexual propagation by tissue culture.

Plant: Under appropriate growing conditions, plants attain a mature size of approximately 10.0 cm to 12 cm in height and approximately 24 cm to 28 cm in width.

Leaves:

*Form.*—The leaf blade is elliptic or obovate with an obtuse to acute apex and a cuneate base. The margins are entire. The midrib is straight over the length of the leaf. The leaf blade is flat or slightly folded upward from the midrib. The upper leaf surface is slightly glossy, more so on newly emerged leaves. The leaves are leathery and thick.

*Size.*—Leaf blades of a mature-sized plant are approximately 14 cm to 16 cm in length and approximately 5.9 cm to 6.4 cm in width.

*Veins.*—Veins are sunken within the thick leaf blade.

*Color.*—Adaxial surface: RHS 137A; newly expanded leaves are RHS 137A tinged with RHS 187A along the leaf margins. Abaxial surface: Greener than, but closest to, RHS 147B, tinged with RHS 187A along the leaf margins.

Inflorescence:

*Description.*—The sepals and petals are white and pink in base color, and are nearly covered with bright pink spots and stripes. The sepals are elliptic-ovate in shape and the lateral petals are broadly ovate with a rounded apex. The sepals and petals are somewhat cupped. The labellum is deeply three-lobed with two prominent callosities at the central junction of the lateral lobes and base of the midlobe. The lateral lobes of the labellum fold upward about the column; the midlobe extends forward and is terminated by two twisted appendages at the apex. The lateral lobes of the labellum are obovate in shape and the midlobe is triangular. The labellum is white in base color with bold spots and stripes of dark red-purple; the callosities are yellow with dark red-purple spots and stripes. The margins of the labellum are tinged with yellow.

*Dimension.*—Overall: Approximately 8.0 cm to 8.4 cm wide and 6.5 cm to 6.9 cm in height. Sepals: Approximately 3.5 cm to 3.9 cm long and 2.5 cm to 2.9 cm wide. Petals: Approximately 3.4 cm to 3.7 cm long and 4.5 cm to 4.9 cm wide. Labellum: Approximately 2.2 cm to 2.5 cm long and 2.3 cm wide (not flattened).

*Flower color.*—Sepals: Adaxial surface: Base color — RHS 155D, and RHS 82C, with RHS 82A–B stripes and RHS 82A speckles. Abaxial surface: RHS 82C, with RHS 82B streaks. Lateral Petals: Adaxial surface: Base color—RHS 155D, and RHS 82C, with RHS 82A–B stripes and RHS 82A–B speckles. Abaxial surface: RHS 155D—RHS 82C–D, with RHS 82A–B stripes. Labellum: Adaxial surface: Base color — white, RHS 155D, boldly striped and speckled with RHS 60A–B and RHS 70A–B. Callosities, RHS 13B, and speckled with RHS 60A. Margin tinged with RHS 13B–C. Abaxial surface: RHS 155D—RHS 82B–C, speckled with RHS 72A–B, with RHS 13C margin.

*Raceme.*—Dimension: The raceme is typically staked upright to a height of approximately 40 cm. The raceme is approximately 56 cm from base to tip and 0.4 cm in diameter at its midpoint. One or two branch spikes containing 3–5 flowers/buds are typically produced. The raceme is RHS 200C tinged with RHS 147B.

*Flowering time.*—For an untreated plant as depicted in Sheet 1 which is flowering for the second time, 8 flowers/unopened buds are present. First flowers can be expected approximately 2–3 months after planting a 12-week-old liner, approximately 3–5 flowers are present.

Reproductive organs: The stamens, style and stigmas are fused into a single, short structure called the column, possessing one terminal anther with pollen grains united into a pollinia, which are covered by an anther cap. The stigma is located under the column behind the pollen. Ovary is inferior with three carpels present.

*Column.*—Approximately 1.1 cm long and 7 mm wide; RHS 155D—RHS 81D in color with markings of RHS 80B.

*Pollen.*—Two, 1.0 mm oval masses of pollen present, RHS 21A.

*Stigma.*—Concave, sticky rectangular, 6 mm×3 mm area under column, RHS 155D.

*Ovary.*—11 mm long and 3 mm in diameter; color is lighter than, but closest to, RHS 82D.

*Pedicel.*—Approximately 2.9 cm long and 4 mm in diameter; color is lighter than, but closest to, RHS 147B tinged with RHS 200C.

Roots: Very thick, greenish-white and fleshy.

Fragrance: None detected.

GENERAL OBSERVATIONS

Plants produce flowers which are almost entirely covered with bright-pink stripes and spots over a white background. The flowers are carried on sturdy, upright, frequently-branched spikes. Mature plants initiate spikes year round, regardless of season, and once in bloom, tend to remain in bloom. The plant grows very easily and quickly to marketable size. The plants grow well, and were selected for tolerance to South Florida conditions which can be extreme for the genus. The plants may experience low temperatures into the mid 40's F., and highs over 104 F.

Pest/disease susceptibility: Typical of Phalaenopsis, no particular sensitivities observed.

I claim:

1. A new and distinct cultivar of Phalaenopsis orchid named 'Dorothy Applegate', as illustrated and described.

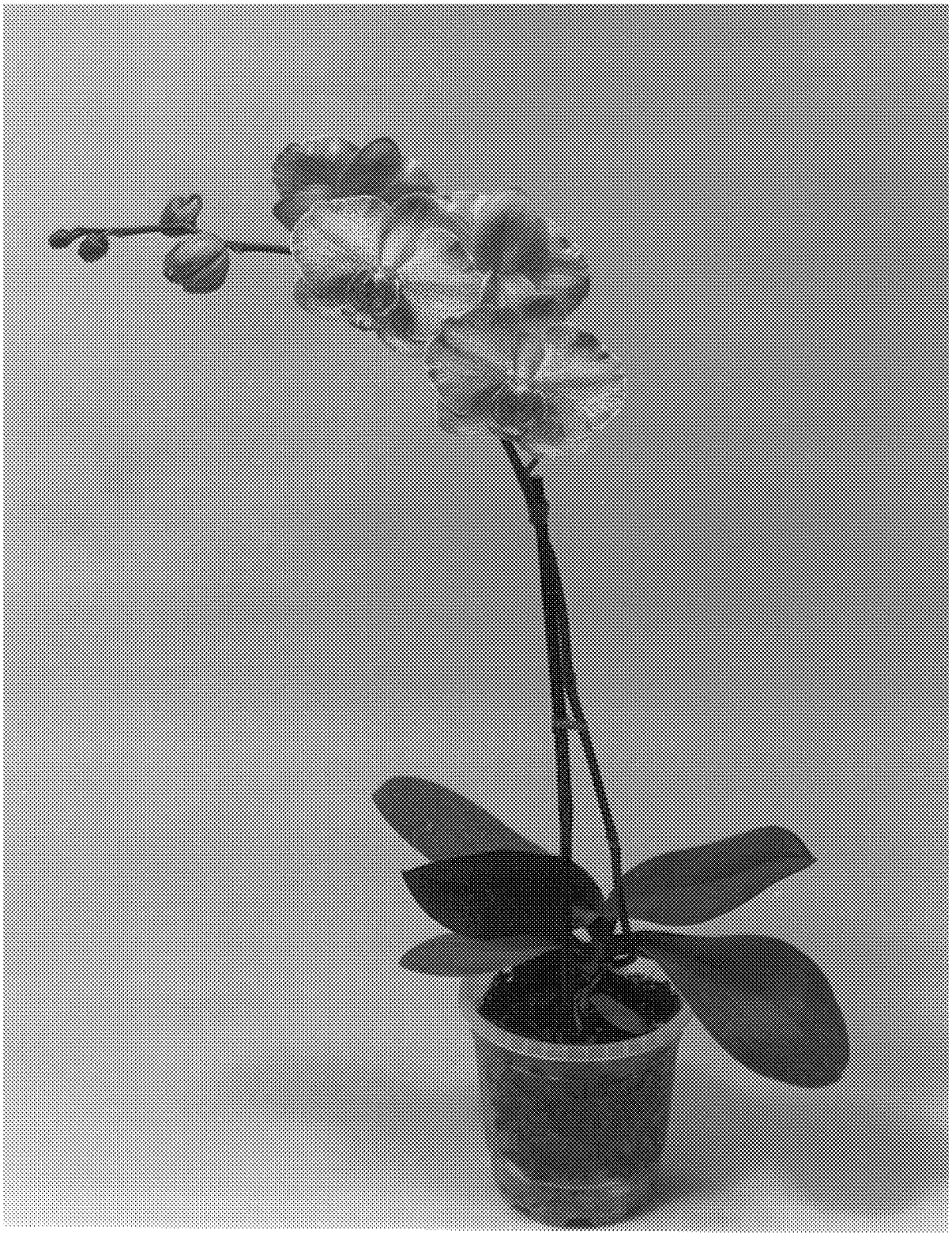

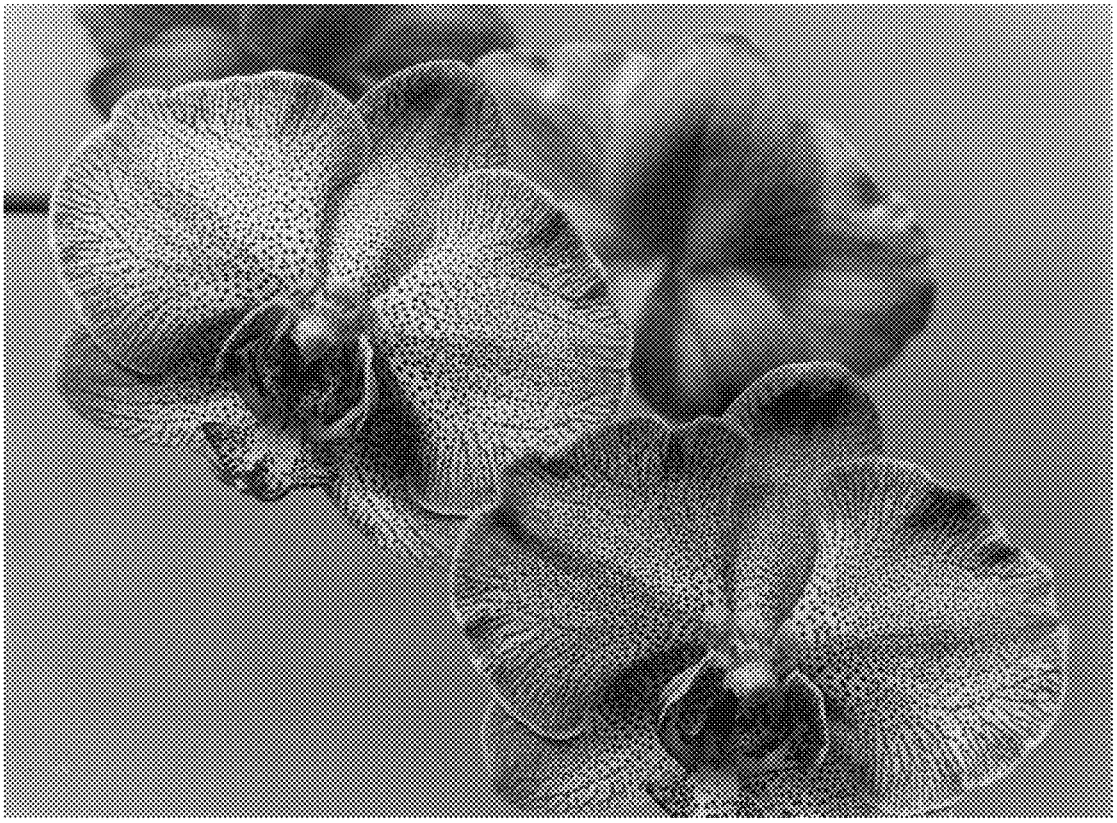

* * * * *